(12) United States Patent
Mitchell et al.

(10) Patent No.: US 10,981,083 B2
(45) Date of Patent: *Apr. 20, 2021

(54) PROCESS FOR FRACTIONATION AND EXTRACTION OF HERBAL PLANT MATERIAL TO ISOLATE EXTRACTIVES FOR PHARMACEUTICALS AND NUTRACEUTICALS

(71) Applicant: Green Extraction Technologies, Brevard, NC (US)

(72) Inventors: Melvin Mitchell, Penrose, NC (US); James Etson Brandenburg, Taylors, SC (US)

(73) Assignee: Green Extraction Technologies, Brevard, NC (US)

( * ) Notice: Subject to any disclaimer, the term of this patent is extended or adjusted under 35 U.S.C. 154(b) by 117 days.

This patent is subject to a terminal disclaimer.

(21) Appl. No.: 16/205,690

(22) Filed: Nov. 30, 2018

(65) Prior Publication Data

US 2019/0151770 A1 May 23, 2019

Related U.S. Application Data

(63) Continuation of application No. 14/454,998, filed on Aug. 8, 2014, now abandoned.

(60) Provisional application No. 61/864,853, filed on Aug. 12, 2013, provisional application No. 61/909,418, filed on Nov. 27, 2013, provisional application No. 61/919,210, filed on Dec. 20, 2013.

(51) Int. Cl.
*A61K 36/00* (2006.01)
*B01D 11/02* (2006.01)

(52) U.S. Cl.
CPC .......... *B01D 11/0211* (2013.01); *A61K 36/00* (2013.01); *B01D 11/0253* (2013.01); *B01D 11/0261* (2013.01); *A61K 2236/00* (2013.01)

(58) Field of Classification Search
None
See application file for complete search history.

(56) References Cited

U.S. PATENT DOCUMENTS

| | | |
|---|---|---|
| 1,951,519 A | 3/1934 | Milne |
| 2,226,429 A | 12/1940 | Hall |
| 2,697,701 A | 12/1954 | Heritage et al. |
| 3,338,416 A | 8/1967 | Barry |
| 4,269,362 A | 5/1981 | Berggren |
| 4,806,475 A | 2/1989 | Gould |
| 4,991,720 A | 2/1991 | Höglund et al. |
| 5,306,392 A | 4/1994 | Mita |
| 5,458,897 A * | 10/1995 | Pare ........................ C11B 9/025 426/241 |
| 5,498,766 A | 3/1996 | Stuart et al. |
| 5,704,559 A | 1/1998 | Fröberg et al. |
| 5,730,837 A | 3/1998 | Black |
| 5,859,236 A | 1/1999 | Burkart |
| 6,156,291 A | 12/2000 | Pang et al. |
| 6,447,815 B1 | 9/2002 | Menon et al. |
| 6,555,074 B1 | 4/2003 | Sweet |
| 6,770,168 B1 | 8/2004 | Stigsson |
| 7,186,423 B2 | 3/2007 | Shan et al. |
| 7,396,434 B2 | 7/2008 | Rodriguez Rivera et al. |
| 7,478,773 B2 | 1/2009 | Gingras et al. |
| 7,504,245 B2 | 3/2009 | Kinley et al. |
| 7,658,955 B2 | 2/2010 | D'Amelio, Sr. et al. |
| 7,678,358 B2 | 3/2010 | Eckert et al. |
| 7,842,161 B2 | 11/2010 | van Heiningen et al. |
| 7,892,397 B2 | 2/2011 | Luo et al. |
| 8,013,195 B2 | 9/2011 | McCall et al. |
| 8,038,840 B2 | 10/2011 | Li |
| 8,268,125 B2 | 9/2012 | Retsina et al. |
| 8,404,884 B2 | 3/2013 | Reaney et al. |
| 8,465,559 B2 | 6/2013 | Guay et al. |
| 8,475,627 B2 | 7/2013 | van Heiningen et al. |
| 8,497,091 B2 | 7/2013 | Hanakawa et al. |
| 8,511,595 B2 | 8/2013 | Lindroos et al. |
| 8,585,863 B2 | 11/2013 | Retsina et al. |
| 8,609,379 B2 | 12/2013 | Chheda et al. |
| 8,741,632 B2 | 6/2014 | Lee et al. |

(Continued)

FOREIGN PATENT DOCUMENTS

| | | | |
|---|---|---|---|
| WO | WO 92/18691 A1 | 10/1992 | |
| WO | WO 2006/111604 A1 | 10/2006 | |

(Continued)

OTHER PUBLICATIONS

Sogi et al. (2010) J. Food Sci. Technol. 47(3): 300-304. (Year: 2010).*
Tang et al. (2004) Natural Product Research and Development vol. 16, No. 3, 231-234. (Year: 2004).*
Wikipedia page entitled "Mixing (process engineering)". Available at https://en.wikipedia.org/wiki/Mixing_(process_engineering). Downloaded from website Sep. 13, 2018. (Year: 2018).*
Banerjee et al, "Alkaline peroxide pretreatment of corn stover: effects of biomass, peroxide, and enzyme loading and composition on yields of glucose and xylose", *Biotechnology for Biofuels* 4(16):1-15 (2011).

(Continued)

*Primary Examiner* — Russell G Fiebig
(74) *Attorney, Agent, or Firm* — Williams Mullen; F. Michael Sajovec; Douglas C. Tsao

(57) ABSTRACT

A process for fractionating a plant material to provide isolated extractives, the process includes pretreating the plant material to provide a fluidized plant material, subjecting the pretreated fluidized plant material to high frequency pulses and shear forces without denaturing bioactive aspects of one or more components of the plant material to provide a first liquid fraction having extractives to be isolated and a first fractionated plant material, separating the first liquid fraction having extractives from the first fractionated plant material, and isolating extractives from the first liquid fraction.

11 Claims, 1 Drawing Sheet

(56) References Cited

U.S. PATENT DOCUMENTS

| | | | |
|---|---|---|---|
| 8,765,846 | B2 | 7/2014 | Balakshin et al. |
| 2002/0132121 | A1 | 9/2002 | Palacio et al. |
| 2002/0148575 | A1 | 10/2002 | Wingerson |
| 2004/0138445 | A1 | 7/2004 | Thorre |
| 2006/0147556 | A1 | 7/2006 | Brewer |
| 2007/0128236 | A1 | 6/2007 | Erskine |
| 2008/0029233 | A1 | 2/2008 | Wingerson et al. |
| 2008/0032344 | A1 | 2/2008 | Fallavollita |
| 2008/0295980 | A1 | 12/2008 | Hallberg et al. |
| 2008/0317661 | A1 | 12/2008 | Eckert et al. |
| 2010/0059609 | A1 | 3/2010 | Teeter, Jr. et al. |
| 2010/0119469 | A1 | 5/2010 | Wu et al. |
| 2010/0167339 | A1 | 7/2010 | Clayton |
| 2010/0325947 | A1 | 12/2010 | Ohman et al. |
| 2011/0003370 | A1 | 1/2011 | Gordon et al. |
| 2011/0024544 | A1 | 2/2011 | Smrha et al. |
| 2011/0100359 | A1 | 5/2011 | North |
| 2011/0313141 | A1* | 12/2011 | Brooks .......... D21C 3/224 530/507 |
| 2012/0108798 | A1 | 5/2012 | Wenger et al. |
| 2012/0197052 | A1 | 8/2012 | Matthews |
| 2012/0282383 | A1 | 11/2012 | Hassan et al. |
| 2013/0005952 | A1 | 1/2013 | Belanger et al. |
| 2013/0202905 | A1 | 8/2013 | Blount |
| 2013/0216520 | A9 | 8/2013 | Medoff |
| 2013/0224816 | A1 | 8/2013 | Elliott et al. |
| 2013/0225855 | A1 | 8/2013 | Ryba et al. |
| 2013/0225856 | A1 | 8/2013 | Ryba et al. |
| 2013/0288307 | A1 | 10/2013 | Medoff |
| 2014/0024093 | A1 | 1/2014 | Blackbourn et al. |
| 2014/0045226 | A1 | 2/2014 | Wicking et al. |
| 2014/0096830 | A1 | 4/2014 | Gastaldo et al. |
| 2014/0121359 | A1 | 5/2014 | Thies et al. |
| 2014/0135470 | A1 | 5/2014 | Murray et al. |
| 2014/0174680 | A1 | 6/2014 | Hawkins et al. |
| 2014/0107353 | A1 | 7/2014 | Qiao et al. |
| 2014/0182801 | A1 | 7/2014 | Hawkins et al. |
| 2014/0190471 | A1 | 7/2014 | Zhang |
| 2014/0196715 | A1 | 7/2014 | Torres et al. |
| 2014/0227742 | A1 | 8/2014 | Bao et al. |

FOREIGN PATENT DOCUMENTS

| | | | |
|---|---|---|---|
| WO | WO 2010/058185 | A1 | 5/2010 |
| WO | WO 2013/144453 | A1 | 10/2013 |
| WO | WO 2013/153203 | A1 | 10/2013 |
| WO | WO 2013/185344 | A1 | 12/2013 |
| WO | WO 2014/046543 | A1 | 3/2014 |

OTHER PUBLICATIONS

Banerjee et al, "Scaled-Up and Integration of Alkaline Hydrogen Peroxide Pretreatment, Enzymatic Hydrolysis, and Ethanolic Fermentation", *Biotechnology and Bioengineering* 109(4):922-931 (2012).

Iyawe et al, "Total Phenolic Contents and Lipid Peroxidation Potentials of Some Tropical Antimalarial Plants", *Eur. J. Medicinal Plants* 1(2):33-39 (2011).

Kim et al, "Front-end recovery of protein from lignocellulosic biomass and its effects on chemical pretreatment and enzymatic saccharification", Bioprocess Biosyst Eng. 36:687-694 (2013).

Sun et al, "Production and extraction of sugars from switchgrass hydrolyzed in ionic liquids", Biotechnology for Biofuels 6(39):1-14 (2013).

Xu et al, "Delignification of Switchgrass Cultivars for Bioethanol Production", *BioResources* 6(1):707-720 (2011).

Notification of Transmittal of the International Search Report and the Written Opinion of the International Searching Authority, or the Declaration corresponding to International Application No. PCT/US2014/050542 dated Nov. 14, 2014.

Notification of Transmittal of the International Search Report and the Written Opinion of the International Searching Authority, or the Declaration corresponding to International Application No. PCT/US2014/050536 dated Nov. 14, 2014.

Notification of Transmittal of the International Search Report and the Written Opinion of the International Searching Authority, or the Declaration corresponding to International Application No. PCT/US2014/050529 dated Nov. 13, 2014.

Notification of Transmittal of the International Search Report and the Written Opinion of the International Searching Authority, or the Declaration corresponding to International Application No. PCT/US2014/050531 dated Nov. 13, 2014.

Bozell, J. et al., Clean Fractionation of Biomass, U.S. Department of Energy by the National Renewable Energy Laboratory.

Du, X. et al., Universal Fractionation of Lignin-Carbohydrate Complexes (LCCS) From Lignocellulosic Biomass: An Example Using Spruce Wood, *Plant J.* Apr. 2013, vol. 74, No. 2; pp. 328-338.

Kumar, P. et al., Methods for Pretreatment of Lignocellulosic Biomass for Efficient Hydrolysis and Biofuel Production, *Industrial & Engineering Chemistry Research*, Mar. 20, 2009, 18 pages.

Li, J. et al., Fractionation and Characterization of Lignon-Carbohydrate Complexes (LCCS) From Eucalyptus Fibers, *Holzforschung*, Nov. 2010, vol. 65; pp. 43-50.

Notification of Transmittal of the International Search Report and the Written Opinion of the International Searching Authority, or the Declaration corresponding to International Application No. PCT/US2015/15378 dated May 14, 2015.

Notification of Transmittal of the International Search Report and the Written Opinion of the International Searching Authority, or the Declaration corresponding to International Application No. PCT/US2015/15368 dated May 18, 2015.

* cited by examiner

PROCESS FOR FRACTIONATION AND EXTRACTION OF HERBAL PLANT MATERIAL TO ISOLATE EXTRACTIVES FOR PHARMACEUTICALS AND NUTRACEUTICALS

CROSS-REFERENCE TO RELATED APPLICATIONS

This application is a continuation of U.S. Utility application Ser. No. 14/454,998 filed on Aug. 8, 2014 that is related to U.S. Provisional Patent Application No. 61/864,853, filed on Aug. 12, 2013, U.S. Provisional Patent Application Ser. No. 61/909,418, filed Nov. 27, 2013, and U.S. Provisional Patent Application No. 61/919,210, filed on Dec. 20, 2013, the disclosures of which are incorporated herein by reference as if set forth in their entireties.

FIELD OF THE INVENTION

The present invention relates to a process of fractionating and/or extracting a plant material, such as an herbal plant material or a tea plant material into its components. Examples of fractions and extractives provided in the process include the extraction, isolation and preparation of extractives useful in pharmaceuticals and nutraceuticals.

BACKGROUND OF THE INVENTION

Plant materials are comprised primarily of cellulose, hemicellulose and lignin, bound together in a complex and entangled gel-like structure along with amounts of extractives, pectins, proteins and/or ash. Thus, successful commercial use of plant material in pharmaceuticals and nutraceuticals depends on the separation of the various constituents, in particular, the separation and isolation of extractives from the other components of plant materials such as hemicellulose, cellulose, and lignin. Many steps are often required in production, harvesting, storage, transporting, and processing of the plant material to yield useful products.

Of particular interest are extractives from plant materials and thereof in the preparation of herbal remedies. Herbal remedies, also sometimes referred to as phytopharmaceuticals or dietary supplements, are becoming increasingly popular as alternatives to conventional pharmaceuticals. Various methods for the isolation and extraction of herbal compounds have been used including, for example, extraction with organic solvents, and isolation by column chromatography and thin layer chromatography. However, these processes are in general not suitable for production scale manufacturing. Production scale processes for the preparation of herbal extracts enriched in components have been described. For example, U.S. Pat. No. 6,447,815 proposes a heated alcohol extraction of herbs and plant material including *Echinacea* wherein higher yields of marker compounds such as alkylamides, may be obtained. However, this method has been found to be unable to separate immunostimulatory and immunosuppressive components found in *Echinacea*. U.S. Pat. No. 7,491,414 proposes a method of producing preparations of *Echinacea* anti-inflammatory and immunosuppressive components including alkylamides, which do not contain immunostimulatory components. U.S. Pat. No. 6,482,432 proposes a process of providing herbal extracts in cellulose derivative capsules, and more particularly, liquid herbal medicaments in vegetable gelatin, hydroxylpropyl methylcellulose (HPMC), or any other cellulose derivative capsules.

There, however, continues to be a need for improved systems and methods for isolating and collecting extractives from plant materials, particularly herbal plant materials that can be done on a production scale.

SUMMARY OF THE INVENTION

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

Thus, the present invention provides a process for fractionating and/or extracting a plant material, and in a particular aspect, the process of the invention provides a process for fractionating or extracting an herbal plant material. The process of the invention is readily adaptable to large-scale production and may be performed at ambient temperature.

The process includes pretreating the plant material to provide a fluidized plant material. The pretreatment may include mechanically altering the fibers and/or contacting the plant material with a solvent. The pretreated fluidized plant material is then subjected to high frequency pulses and shear forces without denaturing bioactive properties of one or more bioactive components of the plant material. This step provides a first liquid fraction having extractives to be isolated and a first fractionated plant material.

DETAILED DESCRIPTION OF EMBODIMENTS

Figure 1:
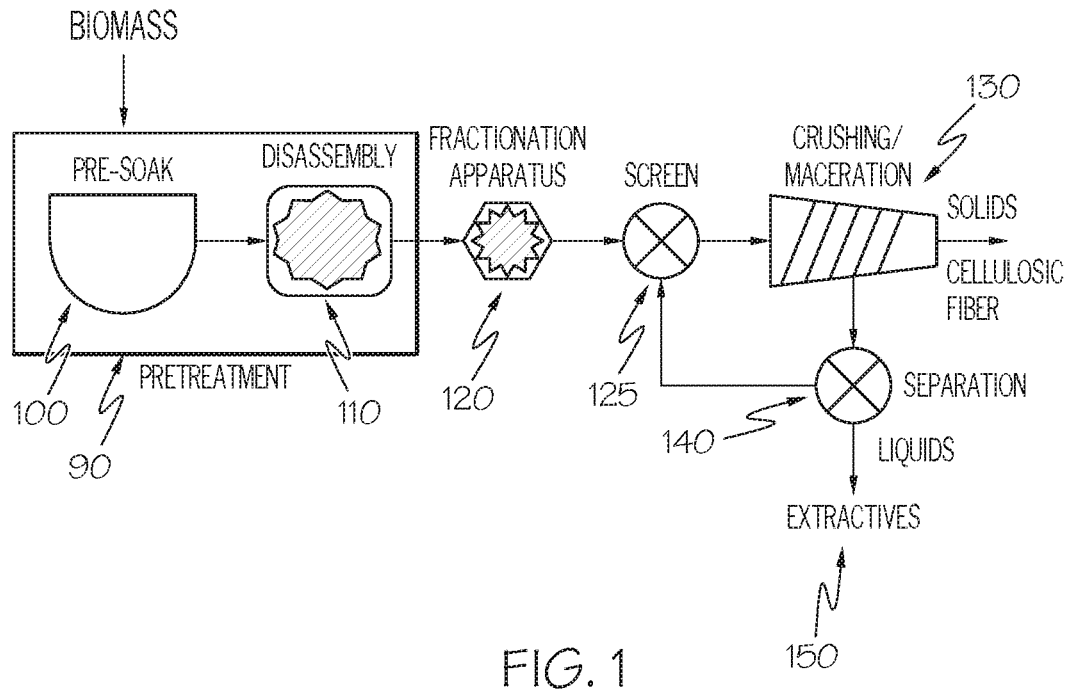
FIG. 1 depicts a flow chart that outlines an embodiment of the process of the invention.

In the following detailed description, embodiments of the present invention are described in detail to enable practice of the invention. Although the invention is described with reference to these specific embodiments, it should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise. The invention includes numerous alternatives, modifications, and equivalents as will become apparent from consideration of the following detailed description.

It will be understood that although the terms "first," "second," "third," "a)," "b)," and "c)," etc. may be used herein to describe various elements of the invention should not be limited by these terms. These terms are only used to distinguish one element of the invention from another. Thus, a first element discussed below could be termed a element aspect, and similarly, a third without departing from the teachings of the present invention. Thus, the terms "first," "second," "third," "a)," "b)," and "c)," etc. are not intended to necessarily convey a sequence or other hierarchy to the associated elements but are used for identification purposes only. The sequence of operations (or steps) is not limited to the order presented in the claims or figures unless specifically indicated otherwise and some steps may be simultaneous.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value, such as, for example, an amount or concentration and the like, is meant to encompass variations of ±20%, ±10%, ±5%, ±1%, ±0.5%, or even ±0.1% of the specified amount. A range provided herein for a measureable value may include any other range and/or individual value therein.

The term "plant material" includes virtually any plant-derived organic matter (woody or non-woody). "Plant-derived" necessarily includes both sexually reproductive plant parts involved in the production of seed and vegetative parts. As used herein, in some embodiments, "plant", "plant part", "plant tissue" are used interchangeably, and for use in the methods of the invention means plant organs (e.g., leaves, stems, shoots, roots, etc.), seeds, plant cells, and progeny of the same. Thus, plant, plant, part, plant tissue also includes, without limitation, protoplasts, nodules, nodes, callus (e.g., embryogenic callus tissue), suspension culture, embryos, as well as flowers, ovules stems, fruits, leaves, side shoots (also referred to as tillers), roots, root tips, and the like originating in plants or their progeny.

In a particular embodiment of the invention, the plant material may be derived from plants that provide materials or extracts with pharmaceutical or nutraceutical characteristics. Such plant material has been described as "herbal plant material." Plant material and herbal plant material subjected to the process according to the present invention can provide materials such as, but are not limited to, lignin, cellulose, hemicellulose, proteins, extractives for pharmaceuticals and nutraceuticals and other extractives or materials obtained from the leaves, stems, flowers, buds, roots, tubers, seeds, nuts, fruit and the like of a plant. The extractives contain the bioactive components of the herbal plant material. Such bioactive components may comprise alkaloids, amaroids, acetogenins, bilobalides, carotenoids, lipids, fatty acids and fatty acid esters, peptides, proteins, lactones, balsams, bitters, camphors, fecula, flavinoids, ginkgolids, isoprenoids, fixed oils, glycosides, gums, mineral compounds, mucilage and pect, saponins, volatile oils, tannins, waxes, and the like.

"Ambient temperature" includes the temperature of the surroundings in which the process of the invention takes place. Ambient temperature may include, but is not limited to, "room temperature," and any temperature within the range of 10 to 40° C. (50 to 104° F.).

"Alcohol" includes, but is not limited to, methanol, ethanol, isopropanol, propanol, isobutanol and butanol. A "short chain alcohol" generally includes $C_1$ to $C_4$ alcohols.

"Water" includes, but is not limited to, deionized water, spring water, distilled water, tap water and well water, and mixtures thereof.

Unless otherwise particularly defined, all technical and scientific terms used herein have the same meaning as commonly understood by one of ordinary skill in the art to which this invention belongs, and all references described herein are hereby incorporated by reference in their entireties for their teachings.

Referring now to FIG. 1, operations for the fractionation and extraction of various plant materials, according to some embodiments of the present invention, will be described. A pretreatment step 90 may be conducted optionally at ambient temperature. The plant material may be subjected to a pre-soak step 100 and/or disassembly step 110. The pre-soak step 100 may include contacting with a solvent with or without agitation. The disassembly step 110 may include mechanical disassembling of the plant material to provide the plant material in a fluidized or flowable state or condition. After the pretreatment step 90, the plant material may be subjected to high frequency pulses 120 and high shear forces to fractionate or extract via, for example, the plant material fractionation apparatus and methods described in co-pending U.S. patent application Ser. No. 14/454,952, filed on Aug. 8, 2014, U.S. patent application Ser. No. 14/454,833, filed on Aug. 8, 2014, and U.S. patent application Ser. No. 14/454,972, filed on Aug. 8, 2014, the disclosures of which are incorporated by reference in their entireties. Such fractionation does not denature the one or more components of the plant material. Stated otherwise, the pulsation and shear forces avoid altering the chemical characteristics of the individual bioactive components. The fractionated or extracted plant material may be subjected to separation, namely filtration or screening 125 with or without agitation, followed by a compression force 130, and then followed by additional filtration, screening, and/or separation with or without agitation 140. The fractions may be used to provide a desired product stream 150 of extractives. It is noted that an initial fraction or extraction product may be collected at earlier points of the method and such previously collected fraction combined with the fraction or extract product stream.

As briefly discussed above, in an initial pretreatment step 90 the plant material may be pre-soaked and contacted with a solvent such as with an alcohol, an aqueous alcohol, water or glycerin or co-solvent or mixture thereof in order to begin the fractionation or extraction of the plant material. The plant material may swell during this pretreatment step 90. The contacting with the solvent and resulting swelling may be facilitated by agitating or shaking to achieve an even distribution of solvent. The plant material may also be disassembled 110 such as by chopping, cutting, fraying, attrition or crushing prior to contact with the solvent 100. In a particular embodiment, if the plant material is, for example, fresh plant or herbal plant material, the material may be contacted with alcohol. If the plant material is dried herbal material, it may be contacted with an aqueous alcoholic solution. This aqueous alcoholic extraction may be performed in aqueous alcohol at different concentrations. Suitable alcohols may be short chain alcohol, such as, but not limited to, methanol, ethanol, propanol, isopropanol, butanol and isobutanol. In a particular embodiment, the alcohol is ethanol. The alcohol may be a co-solvent mixture such as a mixture of an alcohol and water. The aqueous alcoholic solution may comprise from 0-100% (v/v) alcohol. More particularly, the aqueous alcoholic solution may comprise from 25-95% (v/v) alcohol. In a particular embodiment, the aqueous alcoholic solution is 25% (v/v) or more alcohol. In another particular embodiment, the aqueous alcohol may be 60% (v/v) alcohol. In another embodiment, the aqueous alcoholic solution may be 70% (v/v) alcohol. In yet another embodiment, the aqueous alcoholic solution may be 86% or more (v/v) alcohol. In yet other embodiments, the process for fractionating or extracting plant material may comprise contacting the plant material with glycerin or an aqueous glycerin solution. In yet another embodiment, the process for extracting plant material may comprise contacting the plant material with water. Typically, in other embodiments of the invention, the ratio of plant material/solids contacted with a solvent/liquids used may be 1:1 to 1:10 of solids to liquid and in another embodiment may be 1:2 solids to liquid.

With respect to disassembling the fibers 110, the fibers are opened up by chopping, cutting, fraying, attrition or crushing of the plant material and are thereby provided in a fluidized or flowable form. For example, the plant material fibers may be processed in a mechanical high consistency fluidization machine such as a refiner or disk mill. An exemplary disk mill is available from Sprout Waldron, Beloit or Andritz. By utilizing a refiner or disk mill, the plant material and particularly the fibrous material thereof may be altered without destroying the fibrous nature of the fibrous material so that the high frequency pulses and shear forces of the fractionation apparatus are accessible to the fibrous material. The processing may take place for any amount of time necessary as would be understood by one of skill in the art as necessary to affect this step. In a particular embodiment, the disassembly process is performed for one minute or less.

The overall pretreatment step 90 may take place for any period of time that is sufficient for the fractionation or extraction process and may take place in any vessel, container or mixer suitable for contacting the plant material with a solvent and/or disassembling the fibers. In some embodiments, the pretreatment step may be any length of time between, for example, 15 minutes, 30 minutes or one hour, and 72 hours. In another embodiment, the pretreatment step may be 15 minutes or less. The pretreatment step may be one minute or less. In the pretreatment step, the plant material in contact with the solvent may optionally be subjected to a compressive force, which can facilitate absorption of the solvent into the plant material. The compression in the pretreatment step 90 may take place according to any technique that will be appreciated by one of skill in the art. In an embodiment of the invention, compression during the pretreatment step may be affected by a screw press.

The pretreatment step 90 may be conducted at ambient temperature, elevated temperature (30° C. to 90° C.) or using steam/vapor (greater than 100° C.). It is recognized that the vapor may be of the solvent.

Overall the goal of the pretreatment step 90 is to provide the fibers in a form wherein the components of the fibers may be readily fractionated using the high shear forces and pulses of the fractionation apparatus. The selection of the conditions of the pretreatment step 90 such as solvent choice, temperature, pressure, time, additives, and the like will be dependent on the plant material and the components of that plant material to be fractionated and isolated, and will be within the skill of one in the art without undue experimentation.

Following disassembly 110, the plant material is in fluid or flowable form may be subjected to fractionation 120 to fractionate or extract the plant material using shear forces and pulsation. It will be appreciated that in a particular embodiment, shear forces and pulsation are used in which the bioactive components of the plant material are not denatured or altered, and the chemical properties of the individual bioactive components are maintained wherein a portion of the fractions or extracts may be separated from the plant material. The subjecting of the plant material to shear forces and high frequency pulses may take place for any amount of time necessary as would be appreciated by one of skill in the art as necessary to affect this step. In a particular embodiment, this step may takes place for one minute or less. In operation the fluidized plant material is rapidly accelerated from about 4 mph to about 120 mph under greater than 1000 pulses per second of energy while avoiding attrition of the plant material particles. This facilitates the ability of the cellular structure of the plant material to release its various fractions or constituents from the complex and entangled structure of the plant material without having the chemical properties and characteristics of the bioactive components of such fractions being denatured.

The fractionated plant material may then be subjected to a compression force 130 e.g., a crushing or macerating force optionally in the presence of additional solvent, wherein the compression force removes a liquid fraction for collection while discharging a low liquid solids cake primarily being cellulose. The compression force may be applied according to any technique that is appreciated by one of skill in the art. In a particular embodiment, the compression force is affected by screws of a screw press that macerate the fractionated plant material. A second fraction or extract separated from the previously fractionated or extracted plant material may be provided from this compression step. In another embodiment of the invention, the plant material may be contacted with additional solvent and subjected to a second compression force to provide a second extract. The compression of this step may take place for any amount of time necessary as would be appreciated by one of skill in the art as necessary to affect this step. It is recognized that other ways as compared to compression may be used to separate the liquid fraction from the extracted herbal material, e.g., centrifuging, using a membrane or any other suitable separation technique.

The liquid fraction or extract from the previous steps may be combined and filtered or screened 125 with or without agitation to remove any remaining fibers. The filtering/screening of the extracts may be performed by any method known to one of skill in the art with any device that is suitable for filtering and removing any remaining solid matter from the extract. The fractions or extracts provided from the process according to the invention may be used to provide a desired fraction or extractive product stream 150.

Figure 2:
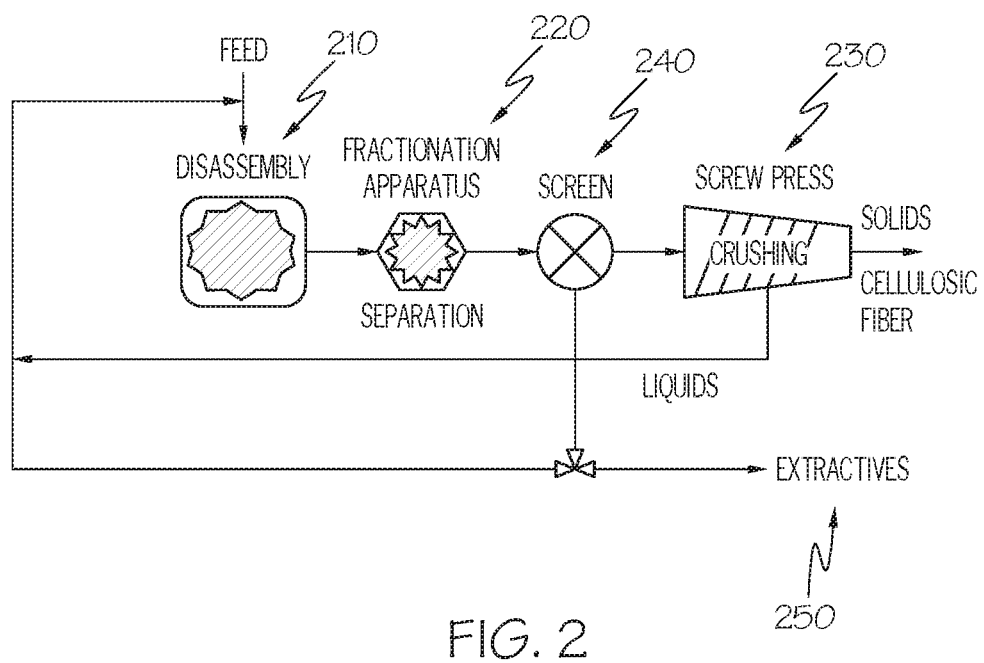
FIG. 2 depicts a flow chart that outlines another embodiment of the process of the invention.

The fractions or extracts provided according to the present invention may be further processed as outlined in FIG. 2. The screened liquids (e.g., liquid fractions) can be contacted with additional plant material, the plant material disassembled 210, fractionated 220, screened 240, subjected to a compressive force 230, and the solid fractionated plant material primarily being cellulosic and the liquid fractionated product stream separated 250. Such a process can be repeated multiple times with the liquid extractive being reapplied to the plant material, disassembled, fractionated, etc., multiple times to isolate or purify the bioactive components of the plant material extractives.

In a particular embodiment, the plant material subjected to the process of the invention is an herbal plant material. The herbal plant material for extraction can be provided in the form of whole leaf, stem, stalk, root, seed, berry and the like, and may be whole, ground or cut prior to treatment. The herbal plant materials can be organic, cultivated, or wild. Suitable sources of herbal plant materials include, but are not limited to, acai, aloe vera, aristolochia, asarium, asian *ginseng, astragalus*, bilberry, bitter orange, black cohosh, butterbur, cat's claw, chamomile, chasteberry, chia, cinnamon, cranberry, dandelion, dong quai, *echinacea*, elecampone, ephedra, european elder (elderberry), european mistletoe, evening primrose oil, unicorn root, fenugreek, tagetes flower, feverfew, flaxseed and flaxseed oil, garlic, ginger, gingko, goldenseal, gota kola, grape seed extract, green tea, hawthorn, hoodia, hops, horse chestnut, kava, lavender, licorice, milk thistle, noni, passionflower, peppermint oil, red clover, red yeast rice, sage, saw palmetto, soy, St. John's wort, tea tree oil, thunder god vine, turmeric, valerian, chia seeds and yohimbe. More particular sources of herbal plant materials may include, but are not limited to: kava kava; *echinacea*; St. John's wort; saw palmetto; holy basil; valerian; milk thistle; Siberian *ginseng*; Korean *ginseng*; ashwagandha root; nettle; ginkgo; gotu kola; ginkgo/gotu kola supreme; *astragalus*; goldenseal; dong quai; *ginseng*; St. John's wort supreme; *echinacea*; bilberry, green tea; hawthorne; ginger, gingko, turmeric; boswellia serata; black cohosh; cats claw; chamomile; dandelion; chaste tree berry; black elderberry; feverfew; garlic; horse chestnut; licorice; red clover blossom and leaf *rhodiola* rusa; coleus forskohlii; eyebright; yohimbe; blueberry plant; black pepper plant; *astragalus*; valerian poppy root and grape seed; *echinacea* ang root; and serenity elixir. In a more particular embodiment, the herbal plant material is selected from the group consisting of gingko leaf kava kava root; milk thistle seed; Korean *ginseng* root; green tea; valerian root; and oregano leaf. In the process of the invention, the herbal plant material may be extracted at ambient temperature without heating.

In another particular embodiment of the invention, the content of the extract of the plant material is an extract of an herbal plant material that comprises a bioactive compound or biomarker. The bioactive compound or biomarker can be the major component to an herbal remedy. During the extraction process, the herbal plant extract derived from the herbal plant material can be monitored for the presence and amount of the bioactive compound or biomarker. As used herein, measuring bioactivity is defined as qualitative and/or quantitative measurement of the bioactive compound biomarker. The methodology for measuring the bioactivity of a compound may change depending upon the source plant material/herbal plant material. The methodology used may be any method accepted or developed by one of skill in the art for the particular bioactive compound desired. The level of bioactivity can be determined using various assays such as GABA assay, GABA benzodiazepine central assay, leukotriane C4 synthetase assay, 5-lipoxygenase assay, monoamine oxidase A assay, and the like.

Suitable bioactive compounds or biomarkers derived by the process according to the invention include:

| Material | Biomarker |
|---|---|
| Ashwagandha Root | Withanolides |
| Astragalus | Total Astragalosides |
| Barberry | Berberine |
| Bilberry | Total Anthocyanins |
| Black Cohosh | Total Triterpene glycosides |
| Black Elderberry | Anthocyanins |
| Black Pepper (Plant) | Piperine |
| Blueberry Leaf | Chlorgenic Acid Derivatives |
| Boswellia serata | Boswellic acids |
| Cinnamon, Organic | Cinnamaldehyde and Phenols |

-continued

| Material | Biomarker |
|---|---|
| Coleus Forskohlii | Forskolin |
| Echinacea angustifolia | Total Isobutylamides |
| Eleuthero | Total Eleutherosides |
| Feverfew | Parthenolide |
| Ginger | Zingiberene |
| Ginkgo | Ginkgo Flavonoid Glycosides |
| Goldenseal root | Total Alkaloids |
| Gotu Kola Leaf | Terpenoids |
| Grape Seed | Procyanidins |
| Green Tea | Total Polyphenols |
| Hawthorn Berries | Total Oligomeric Procyanidins |
| Holy Basil | Eugenol and Rosmarinic acid |
| Kava Kava | Total Kavalactones |
| Korean Ginseng | Total Ginsenosides |
| Licorice Root | Glycyrrhizic acid |
| Milk Thistle | Total Silymarins |
| Olive Leaf | Oleuropein |
| Oregano Leaf | Carvacrol & Thymol |
| Red Clover Blossom & Leaf | Biochanin A |
| Rhodiola Rosea | Total Rosavins |
| Saw Palmetto | Total Fatty Acids |
| Schisandra Berry | Total Schisandrans |
| St John's Wort | Total Hypericins |
| Tagetes Flower | Lutein and Zeaxanthin |
| Turmeric Root | Total Turmerones and Curcuminoids |
| Valerian Root | Total Valerienic Acids |

The use of the bioactive compounds or biomarkers extracted by the process according to the invention is not particularly limited and the use of extracted bioactive compound may be any that would be appreciated by one of skill in the art. For example, extracted bioactive compounds or biomarkers extracted by the process of the present invention may be used as or used in the treatment of, for example, antimicrobials, anti-inflammatories, in the treatment of strains and sprains, antiseptics, indigestion, gastrointestinal disorders, antacids, antivirals, treating cramps, antidepressants, cold treatments, laxatives, arthritis treatment, diuretics, anti-anxiety, appetite regulation, insomnia, headaches, treating acne, treating dermatitis, treating asthma, treating eczema, premenstrual syndrome, fatigue and chronic fatigue, dietary supplements, anticoagulants, astringents, antifungals, antioxidants and the like.

The extractives can be further isolated based on parameter such as solubility, molecular weight range, polarity, adsorption coefficients, binding characteristics, and chemical reactivity. Suitable techniques include pH dependent separations, chromatographic separation techniques, i.e., flash chromatography, preparative high performance liquid chromatography (HPLC), preparative gas chromatography, partition chromatography, preparative thin layer chromatography, affinity chromatography, size exclusion chromatography, liquid-liquid chromatography, e.g., counter-current chromatography or centripetal or centrifugal chromatography, mass spectroscopy (MS) gas chromatography (GS), GS-MS, and NMR. Once isolated from the plant material, the bioactive aspects or components of the extractives can be further isolated and purified. The individual bioactive aspects or components can then be used to provide the pharmaceuticals and nutraceuticals.

The following example is provided to illustrate the present invention, and should not be construed as limiting thereof.

EXAMPLES

Example 1

Ginkgo Leaf 1000 g of ginkgo leaf is chopped and subjected to a pretreatment step of soaking in 60% v/v ethanol for 30 to 90 minutes. 2000 to 9000 g of extract was removed and collected. The slurry of the extracted ginkgo leaf was then subjected to about 3 minutes of activation using a mechanical high consistency fluidization machine. Thus, activated ginkgo leaf slurry is then subjected to high shear forces for 1.5 to 3 seconds of pulses of 1824 to 912 times causing the cellular structure of the ginkgo leaf to release its constituents. The slurry is then subjected to a screw press for less than 3 minutes to provide a liquid extract separate from the solid.

Examples 2-10

The herbal plant materials of Examples 2-10 and the particular biomarker/bioactive material extracted from these herbal plant materials are listed in Table 1, along with the biomarker/bioactive material (ginkgo flavonoid glycosides) extracted and the herbal plant material of Example 1. The biomarker/bioactive material from the herbal plant materials of Examples 2-10 were extracted using the same extraction method of the invention as outlined in Example 1. The quantitative yield of the biomarker extracted for Examples 1-10 by the process of the present invention was compared with the quantitative yield for the lab results using an existing method to extract the same biomarkers from herbal plant material. These results are also depicted in Table 1.

TABLE 1

Comparing Biomarker Yields achieved with invention compared to Lab and Production Methods

| Example | Herb | Biomarker | Raw Material Biomarker Yield Values By Method (mg/g) | | % Biomarker Yield Increase Invention vs. Lab |
|---|---|---|---|---|---|
| | | | Invention | Lab | |
| 1 | Ginkgo leaf | Ginkgo Flavonoid Glycosides | 20.97 | 8.85 | 137% |
| 2 | Kava Kava root | Kavalactones | 148.48 | 69.31 | 114% |
| 3 | Milk Thistle seed | Silymarins | 40.04 | 17.21 | 133% |
| 4 | Black Elderberry | Anthocyanins | 2.66 | 2.33 | 14% |
| 5 | Korean Ginseng root | Ginsenosides | 38.37 | 30.23 | 27% |
| 6 | Green tea | Polyphenols | 138.86 | 134.78 | 3% |
| 7 | Valerian root | Valerenic acids | 2.02 | 1.33 | 52% |
| 8 | Echinacea Ang root | Isobutylamides | 4.16 | 2.69 | 55% |
| 9 | Oregano leaf | Carvacrol | 5.43 | 4.5 | 21% |
| 10 | Ashwagandha root | Withanolides | 2.76 | 1.23 | 124% |

As can be seen from the results shown in Table 1 for Examples 1-10, the process of the invention provides significant improvement in the amount yielded of key biomarkers extracted from herbal plant materials over existing methods.

Although selected embodiments of the present invention have been disclosed for illustrative purposes, those skilled in the art will appreciate that various modifications, additions and substitutions are possible, without departing from the scope and spirit of the invention as disclosed in the accompanying claims.

That which is claimed is:

1. A process for fractionating a plant material to provide isolated extractives, the process comprising:
   a) pretreating the plant material to provide a fluidized plant material;
   b) subjecting the pretreated fluidized plant material to simultaneous high frequency pulses and shear forces without denaturing bioactive properties of one or more bioactive components of the plant material to provide a first liquid fraction having extractives to be isolated and a first fractionated plant material, wherein the high frequency pulses are between about 300 pulses per second and about 2000 pulses per second and delivered over a duration between about 1 second and about 3 seconds;
   c) separating the first liquid fraction having extractives from the first fractionated plant material; and
   d) isolating extractives from the first liquid fraction.

2. The process according claim 1, wherein step d) of isolating comprises contacting the first liquid fraction having extractives with a membrane for selectively isolating the extractives based on molecular weight.

3. The process according to claim 1, wherein the step of pretreating comprises soaking in a solvent selected from the group consisting of water and ethanol.

4. The process of claim 3, wherein the solvent is 50-95% aqueous ethanol.

5. The process of claim 1, wherein step c) of separating the first liquid having extractives from the first fractionated plant material comprises a compressive force applied to the first fractionated plant material.

6. The process according to claim 1, wherein the plant material is a herbal plant material or tea.

7. The process of claim 6, wherein the herbal plant material is in a form selected from the group consisting of whole leaf, stem, stalk, root, seed and berry.

8. The process of claim 6, wherein the herbal plant material is selected from the group consisting of kava kava; *echinacea*; St. John's wort; saw palmetto; holy basil; valerian; milk thistle; Siberian *ginseng*; Korean *ginseng*; ashwagandha root; nettle; ginkgo; gotu kola; ginkgo/gotu kola supreme; *astragalus*; goldenseal; dong quai; *ginseng*; St. John's wort supreme; *echinacea*; bilberry, green tea; hawthorne; ginger, gingko, turmeric; boswellia serata; black cohosh; cats claw; chamomile; dandelion; chaste tree berry; black elderberry; feverfew; garlic; horse chestnut; licorice; red clover blossom and leaf *rhodiola* rusa; *coleus forskohlii; eyebright; yohimbe; blueberry plant; black pepper plant; astragalus*; valerian poppy root and grape seed; *echinacea* ang root; and serenity elixir.

9. The process of claim 1, wherein each of the steps is conducted at ambient temperature.

10. The process of claim 9, wherein the ambient temperature is between 18 to 26° C.

11. A process for fractionating a plant material to provide isolated extractives, the process comprising:
  a) pretreating the plant material to provide a fluidized plant material;
  b) subjecting the pretreated fluidized plant material to simultaneous high frequency pulses and shear forces without denaturing bioactive properties of one or more bioactive components of the plant material by accelerating the pretreated fluidized plant material from about 4 miles per hour to about 120 miles per hour to provide a first liquid fraction having extractives to be isolated and a first fractionated plant material, wherein the high frequency pulses are between about 300 pulses per second and about 2000 pulses per second;
  c) separating the first liquid fraction having extractives from the first fractionated plant material; and
  d) isolating extractives from the first liquid fraction.

* * * * *